United States Patent [19]
Essenpreis et al.

[11] Patent Number: 5,710,630
[45] Date of Patent: Jan. 20, 1998

[54] METHOD AND APPARATUS FOR DETERMINING GLUCOSE CONCENTRATION IN A BIOLOGICAL SAMPLE

[75] Inventors: Matthias Essenpreis, Gauting; Alexander Knuettel, Weinheim; Dirk Boecker, Heidelberg, all of Germany

[73] Assignee: Boehringer Mannheim GmbH, Mannheim, Germany

[21] Appl. No.: 530,241

[22] PCT Filed: Apr. 26, 1995

[86] PCT No.: PCT/DE95/00573

§ 371 Date: Oct. 10, 1995

§ 102(e) Date: Oct. 10, 1995

[87] PCT Pub. No.: WO95/30368

PCT Pub. Date: Nov. 16, 1995

[30] Foreign Application Priority Data

May 5, 1994 [DE] Germany ............... 44 15 728.2
Nov. 8, 1994 [DE] Germany ............... 44 39 900.6

[51] Int. Cl.[6] .................................................. G01B 9/02
[52] U.S. Cl. .................. 356/345; 356/346; 356/39; 250/227.27; 128/633
[58] Field of Search ............... 356/345, 39, 346; 128/633; 250/343, 227.27

[56] References Cited

U.S. PATENT DOCUMENTS

| | | |
|---|---|---|
| 4,632,554 | 12/1986 | Pearce . |
| 4,883,953 | 11/1989 | Koashi et al. . |
| 5,028,787 | 7/1991 | Rosenthal et al. . |
| 5,146,091 | 9/1992 | Knudson . |

FOREIGN PATENT DOCUMENTS

| | | |
|---|---|---|
| 0 074 428 | 3/1983 | European Pat. Off. . |
| 0 160 768 | 11/1985 | European Pat. Off. . |
| 0 426 358A1 | 5/1991 | European Pat. Off. . |
| 0 589 191A1 | 3/1994 | European Pat. Off. . |
| 0 603 658A1 | 6/1994 | European Pat. Off. . |

OTHER PUBLICATIONS

Kruse–Jarres, *J.Clin. Chem. Clin. Biochem.*, "Physico-chemical Determinationas of Glucose in vivo", vol. 26, 1988, pp. 201–208.

International Publication No., WO 93/00856 published Jan. 21, 1993.

Danielson et al., *Applied Optics*, "Guided–wave reflectometry with micrometer resolution", vol. 26, No. 14, 15 Jul. 1987.

Takada et al., *Applied Optics*, "New measurement system for fault location in optical waveguide devices based on an interferometric technique", vol. 26, No. 9, 1 May 1987.

Schmitt et al., *Applied optics*, "Measurement of optical properties of biological tissues by low–coherence reflectometry", vol. 32, No. 30, 20 Oct. 1993.

International Publication No. WO 92/19930 published Nov. 12, 1992.

Huang et al., *Science*, "Optical Coherence Tomography", vol. 254.

*Primary Examiner*—Samuel A. Turner
*Attorney, Agent, or Firm*—Nikaido, Marmelstein, Murray & Oram LLP

[57] ABSTRACT

A method for the analytical determination of the glucose concentration in a biological sample. In a detection step, light is irradiated into the sample and the light emerging therefrom after interaction with the sample emerges therefrom is detected in order to measure a physical light property affected by said interaction. The glucose concentration is determined from this measurement in an evaluation step. To provide a method for determining glucose in reagent-free and non-invasive manner, the invention proposes that a portion of the light emitted by the light source be guided along a reference light path of defined optical path length to the photodetector, that the total measuring light path also has a defined optical length and that the measuring light path after it has traversed the sample is so combined with the reference light path that the measuring light and the reference light interfere with each other. The photodetector measures an interference signal used in the evaluation step to determine the glucose concentration.

46 Claims, 6 Drawing Sheets

METHOD AND APPARATUS FOR DETERMINING GLUCOSE CONCENTRATION IN A BIOLOGICAL SAMPLE

The invention concerns a method for the analysis of glucose in a biological sample and a related glucose measuring apparatus.

The term "biological sample" denotes a body fluid or tissue of a living organism. Biological samples are generally optically heterogeneous, that is, they contain a plurality of scattering centers scattering irradiated light. In the case of biological tissue, especially skin tissue, the cell walls and other intra-tissue components form the scattering centers.

Body fluids, in particular blood, also constitute optically heterogeneous samples because containing particles which scatter the irradiated light. Milk and other foodstuff-chemistry liquids also frequently contain high concentrations of scattering centers, for instance in the form of emulsified droplets of fat.

The invention is suitable for the analysis in comparatively highly scattering, i.e. optically heterogeneous biological samples. However optically homogeneous (that is, low-scattering or entirely non-scattering) samples also may be analyzed by the invention provided suitable embodiments of the invention be employed.

Generally for the qualitative and quantitative analysis in such biological samples reagents or systems of reagents are used that chemically react with the particular component(s) to be determined. The reaction results in a physically detectable change in the solution of reaction, for instance a change in its color, which can be measured as a measurement quantity. By calibrating with standard samples of known concentration, a correlation is determined between the values of the measurement quantity measured at different concentrations and the particular concentration. These procedures allow highly accurate and sensitive analyses, but on the other hand they require removing a liquid sample, especially a blood sample, from the body for the analysis ("invasive analysis"). This blood sampling is unpleasant and painful and includes some risk of infection.

This is foremost the case where a disease requires very frequent analysis. The most important example is diabetes mellitus. To avert serious consequential illness and critical patient conditions, this disease requires determining the blood glucose content very frequently or even continually.

Accordingly a number of procedures and apparatus have been suggested to determine glucose in blood, tissue and other biological samples in vivo and in a non-invasive manner.

A survey of physico-chemical (reagent-free) in-vivo glucose determinations is found in J. D. Kruse-Jarres, J. Clin. Chem. Clin. Biochem. 26 (1988), pp 201–208. Non-invasive procedures described therein include nuclear magnetic resonance (NMR), electron spin resonance (ESR) and infrared spectroscopy. However none of these procedures has achieved practical significance. Large and costly equipment is required, which are wholly unsuitable for routine analysis or even for patient self-checking (home monitoring).

The invention concerns a sub-set of such procedures wherein measuring light from a light source is irradiated as primary light through a boundary surface bounding the sample and wherein light exiting the biological sample through this boundary layer is detected by a photodetector in order to determine a physical light property which is affected by the interaction of light with the biological sample (without using reagents), said property correlating with the glucose concentration in the biological sample. Such a method step is termed hereafter as a "detection step".

The physical light property correlating with the glucose concentration and determined in a detection step (which also may be designated as a quantifiable parameter) is termed hereafter for the sake of simplicity "measurement quantity". However this term should not be understood to require that a particular magnitude of the measurement quantity must be measured in a corresponding dimensional unit.

The methods discussed herein generally do not allow an absolute measurement of the glucose concentration, and therefore (as in the conventional analytical procedures using chemical reactions), calibration is required. Conventionally in at least one calibration step the measurement quantity is determined using a biological sample of known glucose concentration, the calibration step being carried out in the same manner as the detection step. The particular glucose concentration in the sample may be determined by any previously known procedure which allows the determination of the absolute glucose concentration.

In an evaluation step of the analytical method, the glucose concentration is determined from the change of the measurement quantity in at least one detection step in relation to at least one calibration step. The evaluation step includes an evaluation algorithm whereby the glucose concentration is determined in a predetermined manner from the results of at least one detection step.

As a rule the light wavelengths discussed below for such methods are in the range of about 300 to several thousand nm, that is in the spectral range from near ultraviolet to near infrared light. The term "light" may not be construed as being restricted to the visible spectral range.

Nearly all known procedures of this kind are based on spectroscopic principles. The principle is the interaction of the irradiated primary light with the vibrational and rotational states of the analyte molecules. The measurement quantity is the light intensity I which depends from the optical absorption in the biological sample and is determined as a function of the wavelength L. Conventionally the absorptive light attenuation is expressed as $E(L)=\ln [I(L)/I_0(L)]$, with I the intensity of the secondary light and $I_0$ that of the primary light.

The glucose rotational and vibrational ground states are in the IR range at wavelengths exceeding 2,500 nm. Because of the strong absorption by the water always present in high concentrations in biological samples, said ground states cannot be used for non-invasive analysis of glucose. In the range of the near infrared (NIR), water absorption is less (so-called water transmission window). Spectral analysis of glucose in this range is based on the absorption by harmonics and on the combined oscillations of the vibrational and rotational ground states of the glucose molecule (see above cited article by Kruse-Jarres and European patent document A 0426358).

Practical implementation of a glucose sensor based on those principles is very difficult. The signal (i.e. the change in the absorption spectrum as a function of glucose concentration) is very small compared to noise and to interference resulting especially from the water spectral absorption and other strongly absorbing components. Moreover the strong scattering in tissue or blood causes much noise.

Many different attempts have been made to solve this problem. In many cases the solution to the problem of noise interference was sought in a suitable selection of the measurement wavelength jointly with differential measurement. Foremost "two-wavelength spectroscopy" is widely known, wherein a first measurement wavelength is selected in such a way that glucose absorption is as high as possible, the second wavelength being selected as a reference wavelength in such manner that light absorption is affected as little as possible by the glucose concentration. Such procedures, or similar ones, illustratively are the object of the European patent document A 0160768, of WO 93/00856 and of U.S. Pat. No. 5,028,787.

The European patent 0074428 describes a procedure and apparatus using laser light scattering to quantitatively determine the glucose. It is assumed therein that the glucose molecules scatter a light beam transmitted through the solution and that the glucose concentration can be obtained therefrom. According to this theory the solid-angle distribution of the transmitted light intensity exiting a test cell or a tested body part is used as the measurement quantity correlating with glucose concentration. In particular the intensity of the transmitted light is measured in a solid-angle range wherein the change depending on glucose concentration is as high as possible and is then related to the intensity of the central beam passing orthogonally through the sample.

In spite of these endeavors, attempts to make available a non-invasive glucose sensor for practical operation so far have failed.

An object of the invention is to create a method for analytically determining glucose in a biological sample, said method operating in reagent-free and non-invasive manner, and making possible good analytical accuracy, for instance in observing the change in analyte concentration (progress monitoring) over an adequate time interval.

This problem is solved by a method comprising at least one detection step and one evaluation step in the sense of the above discussion, and which is characterized in that part of the light emitted from the light source travels along a reference light path of a defined optical path length to the photodetector, in that the total measurement light path consisting of the primary-side measuring light path, the sample light path and the secondary-side measuring light path has a defined optical path length, in that the secondary-side sample light path and the reference light path are combined before the photodetector in such manner that the secondary light and the reference light interfere with each other whereby the photodetector measures an interference signal and in that the interference signal is used in the evaluation step to determine the glucose concentration.

The invention also refers to a glucose measuring apparatus for the analytical determination of the glucose concentration in a biological sample and comprising a light source to generate the measuring light, light irradiation means comprising a light aperture by means of which the measuring light is irradiated into the biological sample through a boundary surface thereof, a primary-side measuring light path from the light source to the boundary surface, light receiving means for the measuring light emerging from a sample boundary surface following interaction with said sample, and a secondary-side sample light path linking the boundary surface where the measuring light emerges from the sample with a photodetector, said apparatus being characterized in that the light source and the photodetector are connected by a reference light path of defined optical length and in that an optic coupler is inserted into the secondary-side measurement light path which combines the secondary-side measuring light path with the reference light path in such manner that they impinge on the photodetector at the same location thereby generating an interference signal.

An essential element of the invention is the finding that important information concerning glucose analysis may be obtained from the interference between the measuring light and a reference light beam passing along a defined light path outside the sample. The following basic provisions regarding the measurement-technique must be made to generate an interference signal in the sense of the invention.

Interference requires coherence in the interfering partial beams. Light of short coherence length is especially preferred in particularly important embodiments of the invention, and the light source in particular shall be a light-emitting diode (LED) or a superluminescent diode.

The measuring light and the reference light are emitted from the same light source and are detected by the same photodetector. As a rule in interference systems optic couplers are used for splitting light of a single light source into a reference light beam and a measuring light beam which shall be recombined in front of the photodetector.

The total measuring light path (consisting of the primary-side measuring light path from the light source to the sample boundary surface, further of the sample light path traveled by the measuring light inside the sample and of the secondary-side measuring light path from the boundary surface where the measuring light emerges out of the sample to the photodetector) and the reference light path must each have a defined optical path length. A "defined optical path length" in this sense is the condition required for allowing detection and evaluation of interference phenomena.

Detection of an interference signal is only possible if both partial beams interfering with each other are coherent at the detection site (the light sensitive surface of the detector). Therefore both light paths have to be designed in such a manner that coherence is preserved on the way of the light up to the detector. This requires that the distances traveled by the photons between the light source and the detector are sufficiently equal that coherence is not lost to any degree which would spoil the interferometric measurement. The term "(interferometrically) defined optical path length" has to be understood in that sense.

The optical path length is the distance traveled by photons, taking into account the group velocity in the medium. In a homogeneous medium the optical path length $l_0$ is the product of the index of refraction n and the geometric light path length $l_g$ ($l_0 = nl_g$).

An interference signal in the sense of the invention is an electrical signal or signal portion generated by the photodetector and depending on the optical interference between the measuring and the reference lights. Accordingly an interference signal is measured only when interference between the two light portions takes place at the measurement site (the light sensitive surface of the photodetector).

In interferometric measurement procedures, it is conventional practice to use modulation in order to detect in an isolated manner the portion of the detector signal caused by interference. To this end the optical path length of at least one of the light paths (reference light path or measuring light path) is modulated. Conventional modulation may be by means of a piezoelectric transducer (PZT). Modulation causes a small oscillatory change of the light path length (the change in length as a rule is less than the light's wavelength and the modulation frequency ordinarily is in the range of a few tens of kHz). Due to this modulation of the light path length the interference the signal of the photodetector contains an AC component with the modulation frequency. This can be selectively amplified and measured using conventional frequency-selective measurement procedures (for instance the lock-in principle). In this respect "measurement" denotes the reproducible measurement-technical determination of an electrical quantity corresponding to the interference signal. An absolute measurement by which the result may be expressed in a dimensional unit is generally not required.

Interferometric measurement procedures are known for other applications and are widely used. This is especially the case for interferometry using a light source of short length of coherence which is called low-coherence interferometry (LCI). The following publications are referred to in illustrative manner:

Danielson et al: "Guided-wave reflectometry with micrometer resolution", Applied Optics, 26, 1987, pp 2836–2842.

Takada et al: "New measurement system for fault location in optical waveguide devices based on an interferometric technique", Applied Optics, 26, 1987, pp 1603–1606.

Schmitt et al.: "Measurement of Optical Properties of Biological Tissues by Low-Coherence Reflectometry", Applied Optics, 32, 1993, pp 6032–6042.

In these publications both technical objects (fiber optics for information transmission systems) and biological tissue are investigated for their optical properties. The last mentioned literature refers to a three-dimensional imaging procedure. The publications (foremost WO 92/19930) contain a wealth of measurement-technology details which are also advantageously applicable in the present invention, and these are fully incorporated by reference here. However said publications do not convey information or suggestions regarding analysis of the concentration of components in biological samples, in particular glucose concentration.

The interference signal may be used in a number of ways in the evaluation step to determin the glucose concentration. In particular the following three procedural ways are preferred, further details relating to preferred modes of implementation being provided when describing the Figures.

The first of these methods which, in view and present knowledge of the inventors, is the most promising, is based on the finding that the optical path of photons within a biological sample (which also may be termed matrix) depends to an analytically useful extent on the glucose concentration. Using the interferometric procedure, a measurement quantity corresponding to the group velocity of light in the sample, i.e. to the sample's index of refraction, may be determined with high accuracy. This embodiment is explained further below with reference to the Figures.

In a second of said methods, a measurement quantity is determined which corresponds to a change in the scattering cross-section of scattering particles in the biological sample. A reflection apparatus is used for that purpose, wherein light reflected in the sample enters the secondary-side measuring light path. In geometrical terms, the primary-side measuring light path and the secondary-side measuring light path are in the same half space defined by a boundary surface of the sample. Generally in reflection interferometry the same optical elements form the primary-side and the secondary-side measuring light path, that is, light reflected from the sample into the same measurement path is detected. This method moreover requires using a light source of short length of coherence. In order to determine a measurement quantity which is a measure of the scattering cross-section and is characteristic of the glucose concentration the relation of the light path length of the reference light path to the light path length of the reference light path is set to different values. This feature may be implemented by changing the length of the sample light path and/or the length of the reference light path. Changing the reference light path is simpler to implement and therefore preferred. The relationship between the optical path lengths is set in such manner that the interference signal corresponds to different depths in the sample, the glucose concentration being determined from the dependency of the interference signal on the relation between the optical path lengths (that is, from the depth of the sample from which the measuring light was reflected).

In a third method the dependency of the optical-absorption on the light wavelength is determined as the measurement quantity in a manner similar to the above discussed spectroscopic procedures. Within the scope of the invention, the information content of the reference signal is used to determine the optimal light path lengths in the sample. Thereby measurement errors will be precluded which in the hitherto employed procedures were caused mainly by uncertainties concerning the length of the light path inside the sample.

The invention is explained below with respect to illustrative embodiments shown in the Figures.

FIG. 1 is a schematic and block diagram of a reflection interferometer applicable to the invention, FIG. 2 is a graphical representation of experimental results employing the scattering cross-section as measurement quantity.

FIG. 3 is a schematic and block diagram of a transmission interferometer applicable to the invention, FIG. 4 is a highly schematic representation of the human eye to elucidate an embodiment of the invention, FIG. 5 is a schematic similar to FIG. 3 of an experimental model of the anterior eye chamber, FIGS. 6a, 6b are two interferograms from an experiment made with the experimental model of FIG. 4, FIGS. 7a, 7b are Fourier-transformed phase-frequency diagrams from the measurement results of FIGS. 5a, 5b, and FIG. 8 is a plot of the correlation between the empirically determined measurement quantity (phase slope difference) and the glucose concentration.

Figure 1:
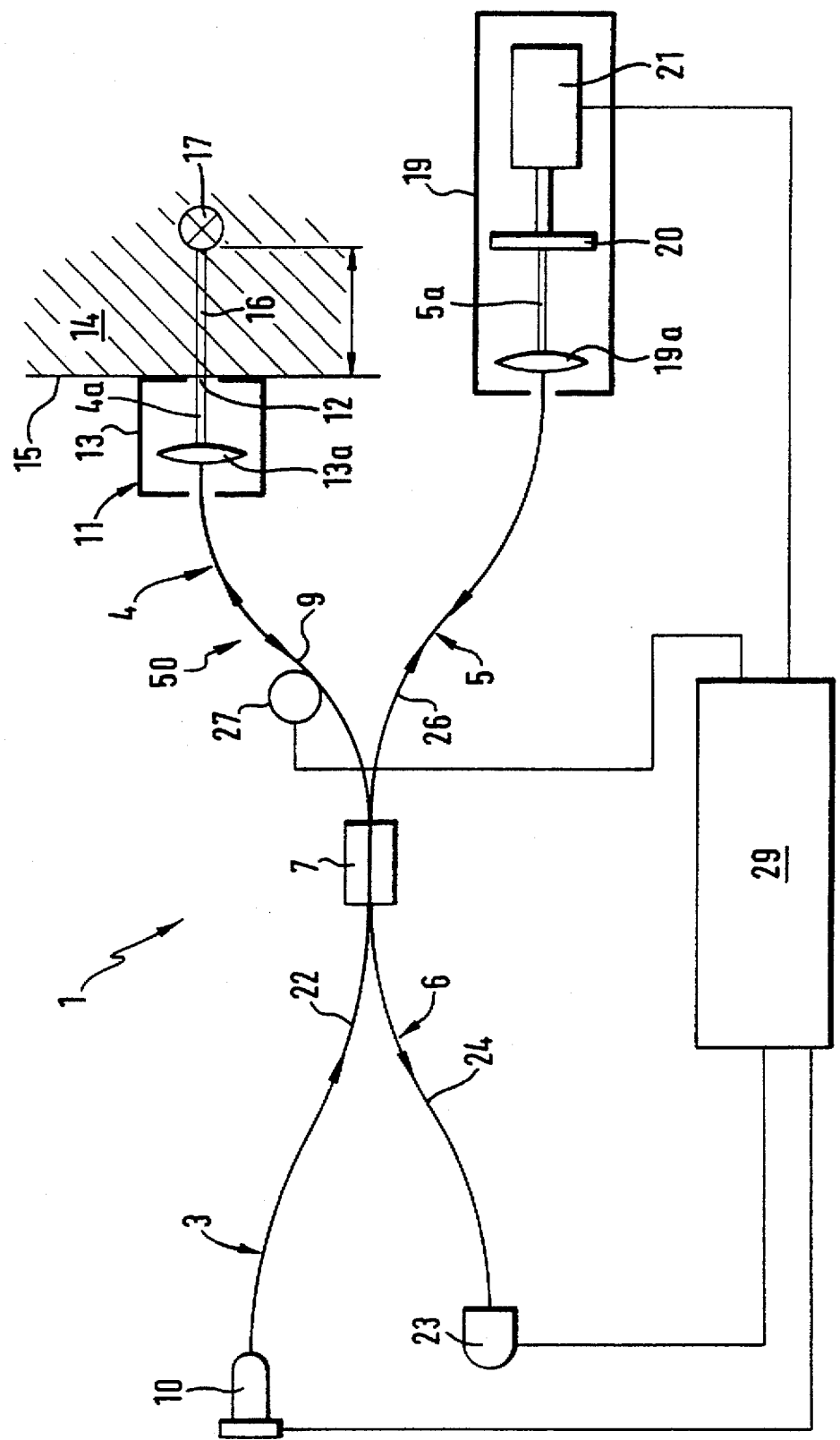

FIG. 1 shows the design principles of a short-coherence reflection interferometer (hereafter also SCRI) 1. It comprises a light source branch 3, a sample branch 4, a reference branch 5 and a detector branch 6, all connected to a light coupler 7.

In the shown preferred embodiment, the interferometer 1 employs fiber optics, that is, the interferometer light paths consist of single mode optical fibers and the light coupler is a fiber-optics coupler.

The measuring light irradiated from a semiconductor light source 10, preferably a superluminescent diode, has a short coherence length (and simultaneously a wide spectral bandwidth) and is fed into an input of the optic coupler 7. The measuring light is guided through the sample branch 4 to irradiation means denoted overall by 11. The irradiation means 11 include a measuring head 13 and a light aperture 12 through which the measuring light is irradiated into the sample 14. The boundary surface crossed by the light entering the sample is denoted by 15.

In an especially important application, the sample is human skin tissue, in particular at the finger pad, the upper abdominal wall, the lip, tongue, inner upper arm, or it is sclera tissue, the tissue surface forming the boundary surface 15. Where the biological sample is a liquid (in particular blood) held in an optically transparent vessel (cell), the boundary surface of the biological sample is the boundary surface between the liquid and the inside vessel wall wetted by the liquid. Herebelow, without implying restriction of general applicability, the sample is considered being skin tissue.

The measuring light entering the sample along a sample light path 16 is reflected by a symbolically shown scattering center 17 toward the measuring head 13. The light which thereby falls into the light aperture 12 of the measuring head 13 passes through the sample branch 4 back into the light coupler 7.

The reference branch 5 is connected to the output side of the light coupler 7 and feeds a part of the light energy radiated by the light source 10 into the light coupler 7 into a reflection system denoted overall by 19. This reflection system contains a reflector 20 (mirror) displaceable along the optical axis and reflecting the incident light to the opposite direction. The reflector 20 is displaceable along the optical axis by means of a linear drive embodied here as an actuator 21.

The light reflected by the sample 14 and the reflector 20 is combined in the light coupler 7 and passes through the detector branch 6 to a light detector 23. Because of the simultaneous presence of the measuring light and the reference light in the same space element (for instance at the detector surface), the condition of spatial coherence is met. Interference takes place when the two light portions fed through the detector branch 7 are also coherent in time.

The primary-side measuring light path 22 which is traveled by the measuring light is the path on which the light is irradiated into the sample 14. In the embodiment of FIG. 1 it consists of the light source branch 3 and the sample branch 4, the secondary-side measuring light path consisting of the sample branch 4 and the detector branch 6. The reference light path overall denoted by 26 consists of the light source branch 3, the reference branch 5 and the detector branch 6. Accordingly, in the shown embodiment, the primary-side measuring light path 22 and the secondary-side measuring light path 24 coincide partly (namely between the optic coupler 7 and the boundary surface 15), whereby both light paths pass through the same optical components.

A requirement for using interference for measurement purposes of the present invention is that the total measuring light path (formed by the primary-side measuring light path 22, the sample light path 16 and the secondary-side measuring light path 24) and the reference light path 26 both have a interferometrically defined optical path length. In the preferred case of using a light source 10 having a short length of coherence (preferably less than 50µ, especially preferred less than 10µ), a further assumption is that the optical path lengths of the total measuring light path and of the reference light path be equal. Otherwise the required coherence in time of the light portions would not be achieved. Thus in the shown embodiment the optical light path from the optic coupler 7 through the sample branch 4 to the reflecting scattering center 17 on one hand and from the optic coupler 7 through the reference branch 5 to the reflector 20 on the other hand must be equal. Only when this condition is met within limits defined by the length of coherence of the light source 10 the photodetector 23 detects an interference signal.

In the shown embodiment a PZT 27 is provided for selectively detecting an interference signal. It modulates the optical path length of one of the partial light paths traveled only by the measuring light or only by the reference light, in the case shown this being the sample branch 4. The PZT 27, the light source 10 and the displacement actuator 21 of the reflector 20 are controlled by a control and measurement electronics 29 to which also the output signal from the photodetector 23 is fed. The measuring circuitry of the control and measurement electronics 29, selectively detects only that portion of the electric output signal from the photodetector 23 which corresponds to the PZT modulation frequency. Electronic measuring procedures providing such functions are known, for instance the lock-in method, and therefore need not be discussed in detail herein.

As already mentioned, interferometric measurement methods and in particular short coherence reflection interferometry (SCRI) are known for other applications. Many variations and measurement techniques are employed such as are described in the above literature. Such variations and techniques also may be used for the present invention on the basis of the stated information. The following description refers to some special applications and alternatives to what has been discussed so far.

The geometric cross-section of single mode fiber optics is so small that they form light paths of defined path lengths, that is, different light paths caused by different reflections at the fiber walls are precluded. In a conventional manner which is also advantageous to the invention, the thin light beam is expanded before it is irradiated into the sample 14 or on the reflecting mirror 20. For that purpose merely symbolically indicated optical components 13a, 19a are provided in the measuring head 13 or in the reflection system 19 of the embodiment of FIG. 1. The expanded light beam forming part of the sample branch 4 or of the reference branch 5 is respectively denoted by 4a and 5a. Both irradiation and detection at the boundary surface 15 of the sample 14 take place in a defined surface segment. The size of these segments must be optimized taking into account signal intensity and resolution of depth-information. Signal intensity demands a larger light transmission site, whereas coherence efficiency drops as the observed site increases. Preferably the diameter of the surface spot through which the measuring light enters the sample 14 and within which the light emerging from the sample is detected by the measuring apparatus is between 0.1 and 1 mm.

In lieu of the fiber optics, a free radiation optics may be used, in which event the optical coupler is a beam splitter. However fiber optics offers an especially compact and economical design.

The modulation technique may be varied in a number of ways. In particular the reflector 20 may be used for modulation by setting it into vibrations corresponding to the frequency of modulation. However this requires a fairly rapid mechanical motion.

It is furthermore possible to use a plurality of different light emitters having different wavelengths or wavelength ranges. The light from different light sources can be coupled by additional light couplers into the measuring light path.

In the shown embodiment, the variation of the relation between the path length of the total measuring light path on one hand and the reference light path on the other is implemented by displacing the reflector 20 along the optical axis of the reference light beam while the sample 14 is located in a defined and constant position relative to the exit aperture 12 of the measuring head 13. Basically however even though more complex, the length of the measuring light paths 22, 24 may be varied instead of the length of the reference light path 26. For instance the measuring head 13 can be displaceable relative to a sample 14 which is in a defined position.

FIG. 1 shows the design principles of a measuring apparatus appropriate for the invention. In a practical embodiment, all the shown components with the exception of the control and measurement electronics 29 are integrated into a single compact measurement module which may be pressed at a defined site at uniform pressure against the skin surface. Advantageously, the temperature at the particular measurement site may be kept constant, or it may be measured in order to take it into account in the evaluation step for determining the glucose concentration.

The shown short-coherence reflection interferometer allows to measure in a controlled manner interference signals reflected from a defined depth of the sample 14. As a result the measurement can be directed to tissue which is located relatively deep inside the body, for instance the retina. As already mentioned, the presence of an interference signal at the detector 23 requires that the light path in the sample branch inclusive the sample light path 16 and the light path in the reference branch 4 are of equal length (maximally deviating from one another by the length of coherence). To allow depth scanning, the interferometer is designed in such manner that the shortest optical path length of the reference branch 5 set during operation is somewhat shorter than the optical path length of the sample arm 4 (from the light coupler 7 to the boundary surface 15). If, starting from this position, the length of the reference branch is increased by moving the reflector 20 (from left to right in FIG. 1), then the Fresnel reflection occurring at the boundary surface 15 causes a strong signal peak when the said optical path lengths are the same. Upon further lengthening of the reference branch 5, the reflection point 17 in the sample 14 shifts toward greater depths, that is, the sample path 16 increases, the optical path length of the sample path 16 corresponding to the difference between the optical path lengths of the reference branch 5 and the sample branch 4.

An interference signal can be detected by the detector 23 only if a reflecting scattering center 17 is present at the corresponding depth in the sample 14. In biological samples the density of scattering structures is so high, however, that light is reflected virtually for any setting of the depth scan. Obviously the high density of the scattering centers and the presence of absorbing substances in the biological sample 14 causes loss of the major portion of the irradiated light by absorption or by scattering due to scattering centers in the light path. Short coherence reflection interferometry however makes it possible to selectively detect only those photons which travel unscattered up to the reflecting scattering center 17 and back to the boundary surface 15. All other light portions do not meet the coherence condition and therefore are not detected as interference signals.

The analytical glucose concentration in the sample may be determined using the measurement system shown in FIG. 1, by means of the three methods discussed in principle above, as follows:

The variable depth-scan is advantageously employed to determine a measurement quantity corresponding to the index of refraction using a reflection system as shown in FIG. 1. The variation in optical path length of the reference light path relative to the optical path length of the measuring light path should be larger than the mean free path of light in the sample. Preferably it shall be a multiple of the mean free path (for instance 1 or 2 mm), whereby the reflection point is shifted over a plurality of scattering centers during depth scan. The interference signal has a characteristic structure depending on the scan depth. This interference-signal structure documents the optical path length between the scattering centers generating the structure. Accordingly the spacing between structural features (for instance the peaks) of the interference signal is affected by a change in index of refraction caused by the change in glucose concentration. Illustratively therefore the spacing between two specific peaks in the interference-signal structure (intensity over scan depth) is a measure of glucose concentration. This spacing may be determined from the interference-signal structure. In practice preferably not a specific spacing between two given peaks, but rather the entire information contained in the said structure is analyzed using image-analysis procedures and is evaluated by means of suitable numerical methods.

Preferably the depth scan is carried out in an oscillating manner, the setting curve of the reflector for instance being triangular, serrate or sinusoidal. The data are collected over a large number of oscillations to improve the signal-to-noise ratio.

Preferably the measurements are carried out at a plurality of different wavelengths of the measuring light. Additional information may be gained when measuring at various wavelengths because the index of refraction depends on the wavelength. In a simple illustration, two wavelengths may be used to increase the accuracy of measurement, one being selected in a wavelength range where the index of refraction strongly depends on the glucose concentration while the other is in a range of minimum dependence of the index of refraction on the glucose concentration.

The magnitude of the change of the optical path length caused by a change of the glucose concentration in the physiological range may be estimated as follows. A 1 mM change in glucose concentration relates to a change in index of refraction of about 0.002%. For a total length of the sample light path of about 2 mm (1 mm depth of penetration in the sample 1), the optical path is changed by about 40 nm. At a measuring-light wavelength of 800 nm, the corresponding phase shift is about 18°. This change can be determined with sufficient precision that an adequate measurement accuracy is achieved to monitor the glucose level of diabetics.

When the second method of determining the glucose concentration from an interference signal is used, a measurement quantity is determined which corresponds to the scattering cross-section of scattering centers in the sample. To this end the intensity of the interference signal I is determined at different lengths of the sample light path 16, that is, at different depths of penetration x. For that purpose the length of the reference light path 26 is set at different values by axially displacing the reflector 20. In practice this is again performed in an oscillating manner. At various settings of the reflector 20, automatic measurements are triggered to determine the dependency I(x) of the intensity I on the depth of penetration x within a desired range. For maximum accuracy of measurement, the function I(x) should be measured over as large a range of the depth of penetration x as possible. In practice, using acceptable intensities, according to the present state of experimental work a depth of penetration of about 2 mm is feasible. The larger the scanned range of depth of penetration, the larger the geometrical length scanned and hence the accuracy of measurement. In many applications however it may be desirable to scan only over a smaller range of depths in order to determine the glucose concentration at a given depth below the skin surface.

The correlation between the scattering cross-section and the glucose concentration can be explained in that the scattering cross-section in the heterogeneous tissue system depends on the relation between the index of refraction of the scattering centers and the index of refraction of tissue fluid. If the latter index of refraction changes because of a change in glucose concentration, then the scattering cross-section changes to.

In the above described measurement method, the computation of the glucose concentration from the measurement quantity I(x) can be carried out by explicitly calculating the scattering cross-section, as described in the above publication by Schmitt et al. In practice however preferably a numerical correlation procedure is used, wherein all the acquired measurement data are correlated by calibration with glucose concentrations (known from conventional measurements). Illustratively the conventional partial least squares (PLS) procedure is used for that purpose.

Figure 2:
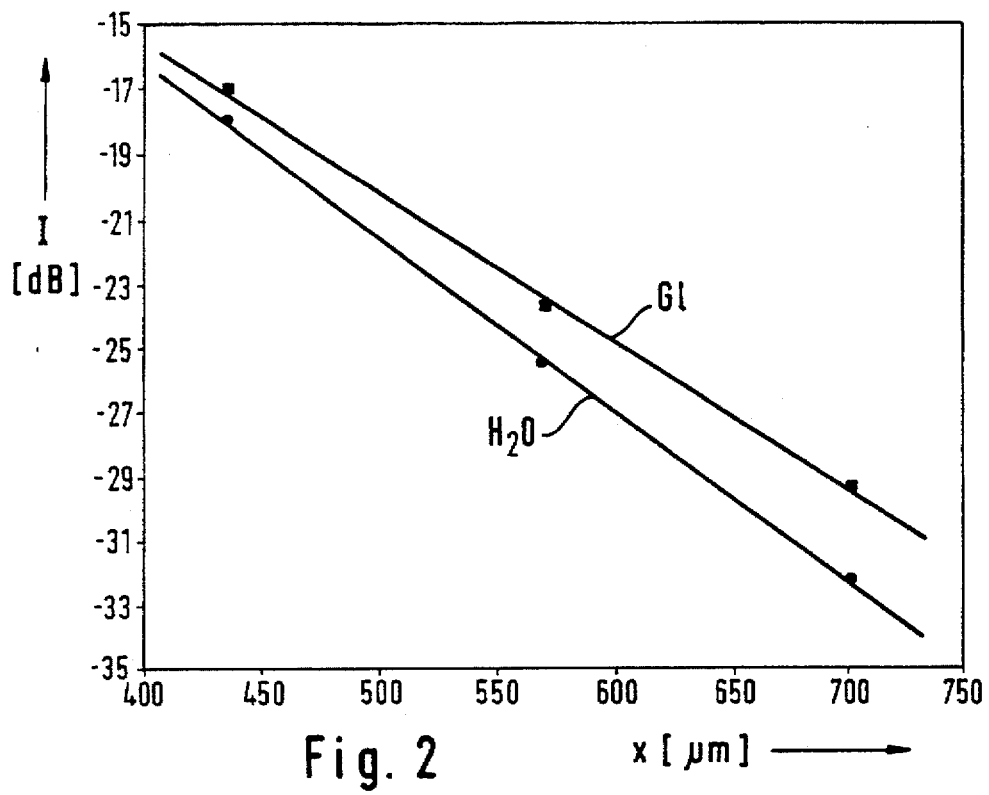
Figure 8:
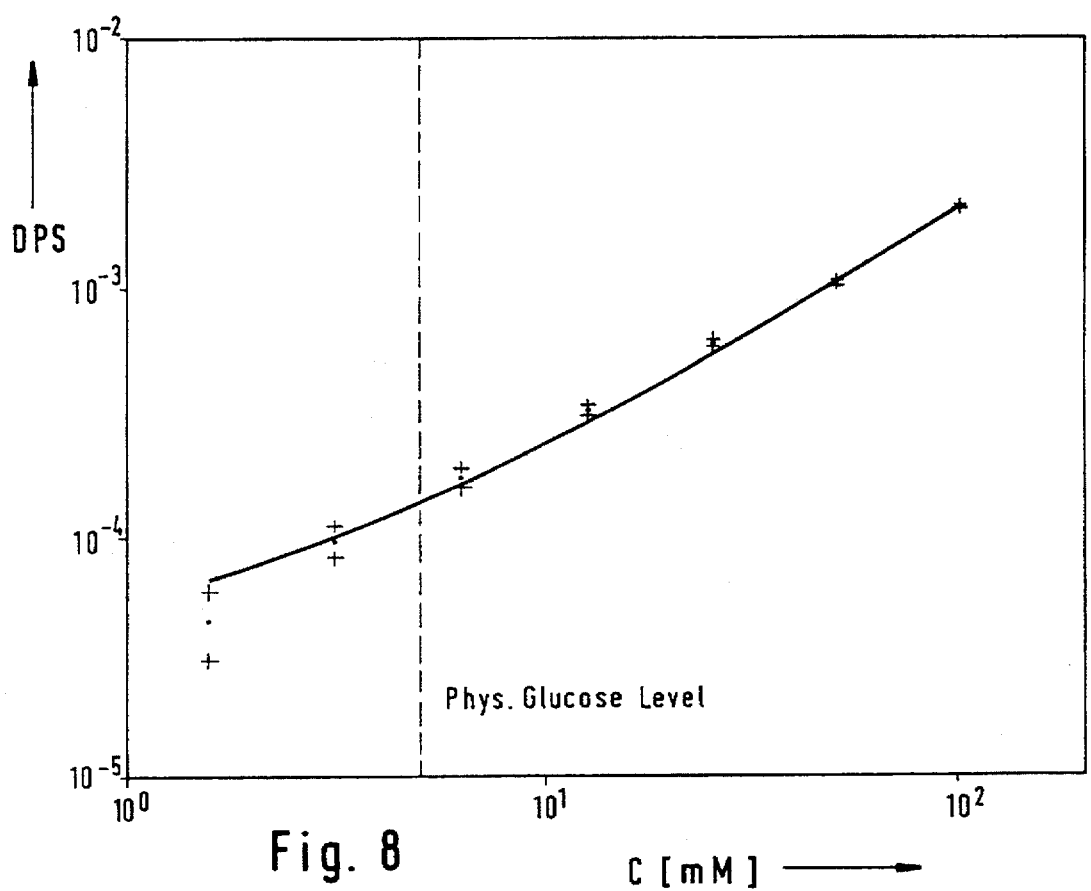

FIG. 2 shows experimental results on the basis of this method. The measurements were made with an experimental model of the skin consisting of a scattering solution of latex particles with a solid content of 2.5 weight % and a cross-section of 0.2 μm. In this liquid a depth scan was performed as described above using a SCRI corresponding in principle to FIG. 1. FIG. 2 shows the dependence of the measured intensity variation (in dB) from the penetration depth x. The lower straight line represents measurement results with pure water ($H_2O$), while the upper straight line shows results with 400 mMol glucose solution (Gl= glucose). It becomes apparent that the measurement quantity I(x) changes substantially in dependence on the glucose concentration.

When using the third method, information on the dependency of the interference signal I on the depth of penetration x is not mandatory in order to ascertain the spectral dependency of the interference signal for the determination of the glucose concentration. In other words, a constant setting of the path length of the reference light path 26 may be used (as also in the determination of the glucose concentration on the basis of the index of refraction). However it may be advantageous to secure additional information by repeating the measurement with different path lengths of the reference light path and accordingly different lengths of the sample light path 16.

As already stated, the actual analysis is based in this method on known spectroscopic principles. Illustratively—as for the case of two-wavelengths spectroscopy—two different wavelengths of the measuring light may be used, one measuring wavelength $L_1$ being selected within a wavelength range wherein absorption is strongly dependent on glucose concentration, whereas at a second wavelength $L_2$, denoted the reference wavelength, the dependency of the absorption on the glucose concentration is as little as possible.

A substantial source of error of prior art methods, namely the lack of knowledge of actual light path or the fact that different light paths in the samples must be taken into account at different wavelengths, is avoided by the invention because it uses the interference signal of an SCRI procedure as the basis of the spectral analysis. In spectroscopy the optical path length traveled by the detected light inside the sample should be constant or at least reproducible. In the method of the invention this is accomplished because the particular "cell length"—that is the sample light path traveled by the light in the sample, is defined by the actual setting of the light-path length of the reference light path.

Figure 3:
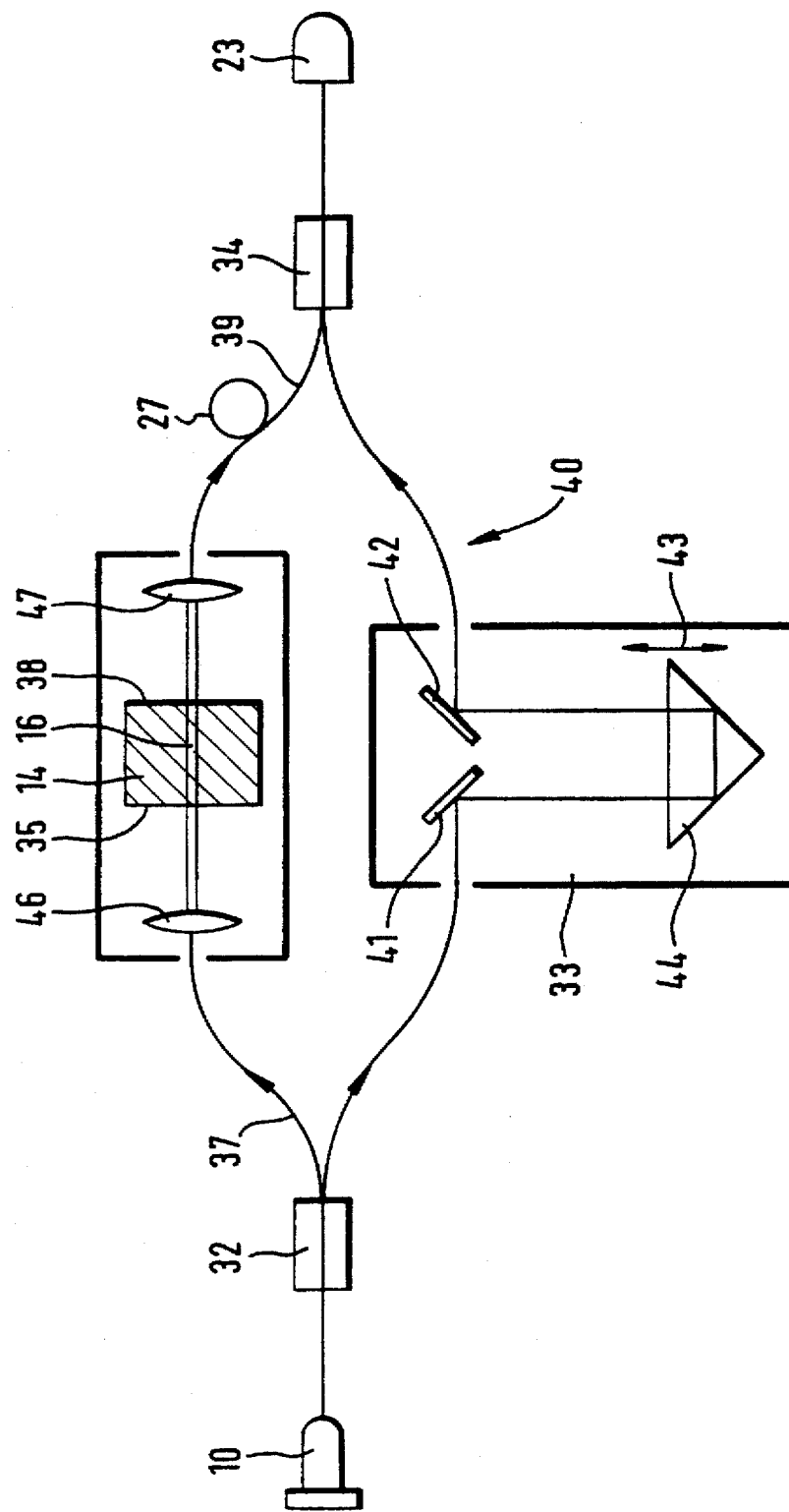

FIG. 3 shows a transmission interferometer wherein the light is not reflected by the sample 14 but instead is transmitted through it. Such a system is applicable to investigate thin layers of biological fluids or also to determine in-vivo the glucose at corresponding thin skin folds (between the fingers or at the ear lobe). Measuring light is fed from a light source 10 to a first light coupler 32 splitting the light energy into two portions, a first portion being further guided to the sample 14 and a second portion being guided to a reference system 33 with defined and preferably adjustable light path length.

The measuring light emerging from the sample 14 is fed to a detector 23 via a second light coupler 34. The measuring light and the reference light from the reference system 33 are combined at the light coupler 34.

The path of the measuring light from the light source 10 through the first light coupler 32 up to the front boundary surface 35 of the sample 14 is termed the primary-side measuring light path 37. The light path from the rear boundary surface 38 (at which the light having traveled the sample light path 16 in the sample 14 emerges therefrom) to the photodetector 23 is called the secondary-side measuring light path 39. The light path from the light source 10 through the first light coupler 32, the reference system 33 and the second light coupler 34 up to the photodetector 23 constitutes a reference light path 40. The length of the reference light path 40 is adjustable. Adjustment may be implemented for example as indicated in the figure by two mirrors 41, 42 and a prism 44 displaceable in the beam direction 43. As in the embodiment of FIG. 1, a modulating PZT 27 is mounted in one of the light paths, in the shown example in the secondary-side measuring light path 39. Optical components 46, 47 respectively expand the beam in front of the sample 14 and couple the secondary side measuring light into the fiber optics forming the major part of the secondary-side measuring light path 39.

In a transmission system as shown in FIG. 3, the geometric light-path length of the sample light path 16 in the sample is fixed. A change in the index of refraction in the sample 14 leads to a change of the optic light path length. This change can be directly measured with the shown system. If a light source 10 with short-coherent light is used and if at a first glucose concentration the length of the reference light path 40 is set in such manner that an interference signal is measured at the detector 23, then the total measuring light path consisting of the primary-side measuring light path 37, further by the sample light path 16 and the secondary-side measuring light path 39, has the same optical path length as the reference light path 40. If thereafter the glucose concentration and thereby the optic light path length of the sample light path 16 changes, a length adjustment in the reference light path is required to maintain the interference signal, and said adjustment is a direct measure of the glucose concentration.

When using a light source 10 of large length of coherence, for instance a laser, the measurement of the change of the optical path length of the sample light path 16 is also possible, in particular by measuring the phase shift between the modulation signal fed to the PZT 27 and the corresponding modulation of the interference signal.

Lastly in a system of FIG. 3 the glucose concentration again may be determined from the spectrum of the interference signal. Preferably both in the system of FIG. 1 or in that of FIG. 2 this is not performed by means of spectral splitting of the primary light (for instance by coupling in the light of several different LED's). Rather only one light source 10 is used which has a broadband spectrum covering the full desired range of wavelengths. The path length of the reference light path 26 or 40 is changed in oscillatory manner (by moving components 20 or 43) and from the interference patterns so obtained, the spectral dependency is computed by means of known Fourier-Transform spectroscopy.

In a preferred embodiment of the invention, to be elucidated below in relation to FIGS. 4 through 8, the biological sample includes the aqueous humor in the anterior-chamber of the eye. Preferably the measurement is restricted to the anterior chamber only, though it is also feasible to include further (deeper) parts of the eye in the measurement.

The possibility of determining the glucose concentration in the eye's anterior chamber using an optical property of the aqueous humor depending on this glucose concentration has already been long discussed. For instance the 1976 U.S. Pat. No. 3,958,560 describes the possibility to irradiate light from one side of the anterior chamber at a shallow angle into said chamber in such manner that the beam passes straight through the anterior chamber along a secant to the cornea curvature and exits on the far side (again at a shallow angle) ("anterior-chamber transmission method"). Procedures wherein the light is irradiated from the front (approximately normally to the cornea curvature) into the anterior chamber and wherein light reflected out of this chamber is detected ("anterior-chamber reflection method") illustratively are known from the European patent applications 0 589 191 and 0 603 658. The measurement quantities discussed in these publications are the optical rotation of polarized light and the (spectroscopically measured) optical absorption.

Within the scope of the present invention use of anterior-chamber transmission is also possible in which case the measurement techniques of FIG. 3 are used. Preferably however an anterior-chamber reflection method using a short-coherence reflection interferometer (SCRI) such as illustratively shown in FIG. 1 is used. Preferably again a measurement quantity of light is measured which corresponds to the index of refraction of the aqueous humor in the anterior chamber. For this embodiment it is advantageous that the aqueous humor in the anterior chamber is optically homogeneous and thereby the light is practically not scattered therein.

Figure 4:
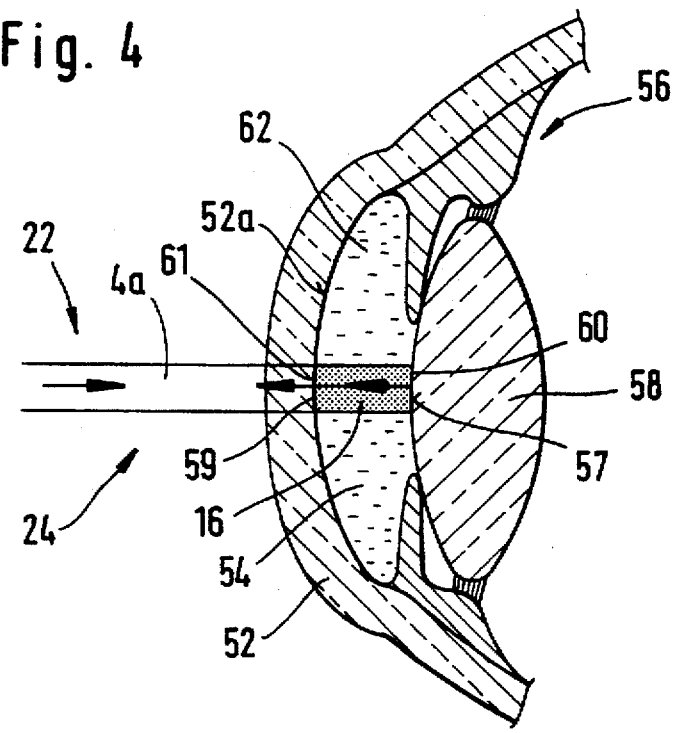

The principle of the measuring system is shown in FIG. 4. The primary-side measuring light path 22 is such that the measuring light is incident from the front (in geometric terms at an acute angle to a surface normal of the cornea 52) and enters the anterior chamber 54 of the eye 56. The light reflected back inside the eye, in particular at the surface 57 of the lens 58, again crosses the cornea 52 at a nearly right angle (more precisely, at an acute angle to a surface normal of the cornea 52) and coincides with the secondary-side measuring light path 24.

As already mentioned, preferably a short-coherence reflection interferometer with the main features shown in FIG. 1 is used in this embodiment. As shown in FIG. 1, in an especially preferred embodiment, the primary-side measuring light path 22 and the secondary-side measuring light path 23 coincide in the sample branch 4 leading to the sample (i.e., the sample branch 4 is common to both measuring light paths). In this instance the light path segment in front of the eye 56 is appropriately formed by the expanded light beam 4a of the sample branch 4. During the reflection measurement at the eye shown in FIG. 3, the sample light path 16 passes through the aqueous humor 62 contained in the anterior chamber 54 from a light entry site 59 to a reflection site 60 and then in the opposite direction to a light exit site 61. The boundary surface 15 is formed by the inside surface 52a of the cornea 52 that faces the eyeball. In the shown embodiment comprising a common sample branch 4 for the primary-side measuring light path 22 and the secondary-side measuring light path 24, the entry site 59 and the exit side 61 are at the same place of the cornea 52. Basically, even if less preferred, however an optical system may be used for which the sample branch 4 of the primary-side measuring light path 22 and of the secondary-side measuring light path 24 is not common, as a result of which the entry site and the exit site of the measuring light are located at different places of the cornea 52. In this case the sample light path between the entry site and the reflection site also does not coincide with the sample light path between the reflection site and the exit site. Such a beam guidance is illustratively described in the European patent document 0 603 658 A1.

Figure 5:
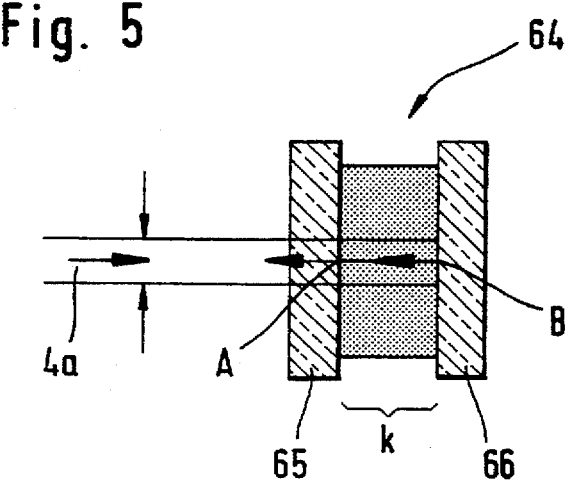

The experimental model shown in FIG. 5 is designed in such manner that the essential boundary conditions correspond to human-eye measurements. The measuring light from a sample branch 4 of a SCRI and with a diameter for instance of 50μ is irradiated into a cell 64 simulating the anterior chamber 54. The entry boundary surface 15 in this instance is formed by the inner surface of the front cell glass 65, the reflection site 60 being located at the inside surface of the rear cell glass 66. A cell length k of 1 mm was selected in practical experiments. As a result the round-trip length of the sample light path 16 is 2 mm. In the human eye, the thickness of the anterior chamber is about 3 mm, and therefore the total length of the sample light path 16 is 6 mm. In this respect the experiments of the experimental model shown in FIG. 5 were carried out under more difficult conditions.

Figure 6B:
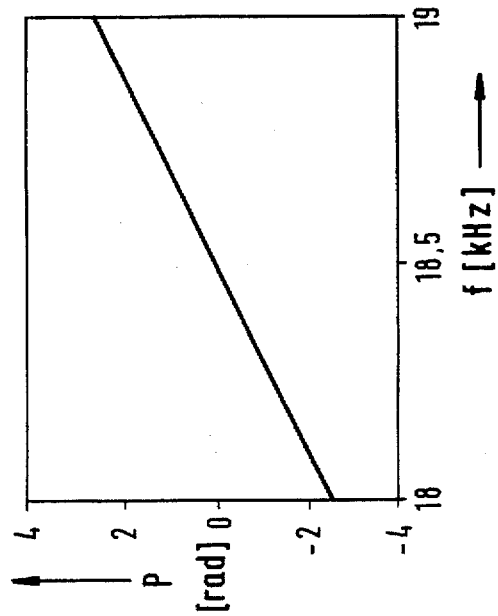
Figure 6A:
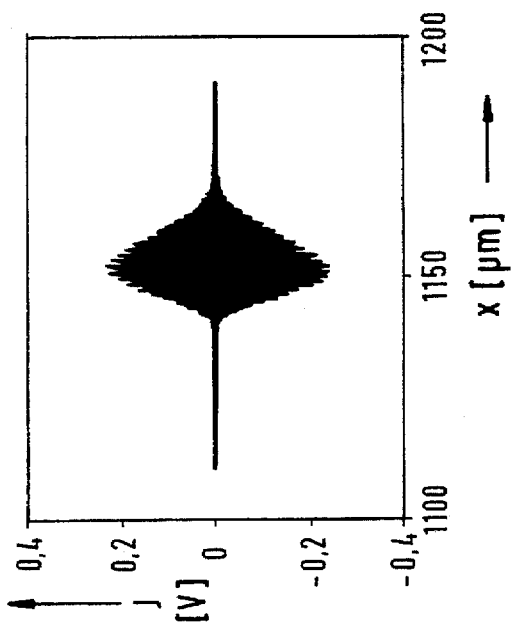

The interferograms shown in FIG. 6 were measured on an experimental model of FIG. 5 under the following measurement conditions.

Essentially the SCRI design was that of FIG. 1. The light source was a 0.5 mw superluminescent diode with a central wavelength of 850 nm. The cell 64 was made of Suprasil quartz glass and was filled with glucose-water solutions of different concentrations. The initial glucose concentration was 100 mM and the concentration was then halved from measurement to measurement down to 1.56 mM. The temperature inside the cell was thermostatically regulated to 22° C.±1° C. The reflector 20 was a corner cube reflector oscillating at a speed of about 7.9 mm/s. The possibility of carrying out a depth scan and simultaneously providing modulation of the path length by means of a reflector moved in an oscillating manner was already discussed in relation to FIG. 1. The drawback mentioned at the time concerning a relatively rapid mechanical motion of the reflector 20 is comparatively minor when performing measurements on the eye because of the comparatively shallow total scan depth (thickness of the anterior chamber).

Data acquisition software was used to evaluate the interferogram. It allowed to select two partial zones (windows) in the vicinity of the main reflections within the total depth-scan range, said main reflections taking place at the rear surface of the front cell glass 65 and at the front surface of the rear cell glass 66. These reflection points are denoted by A and B in FIG. 5. In the natural eye they correspond to the entry site 59 (boundary surface between cornea and aqueous humor) and to the reflection site 60 (boundary surface between the aqueous humor and the lens).

In the experimental model of FIG. 5, the distance between these two reflections of maximum intensities is 1 mm. Accordingly interferograms arise in the two windows of the scan depth shown in FIG. 5 (the length scale has an arbitrary zero point) at about 150μ and at about 1,150μ, that is a distance of 1,000μ apart.

Information concerning the optical path length of light between the reflection points A and B may be generated from the interferograms of FIG. 6 as follows:

The interferograms of FIG. 5 are digitized and subjected to Fast Fourier Transformation (FFT) by a digital signal processor (DSP). The moduli of the transformed results are discarded. Only the phase results are processed further. As shown in the publication W. L. Danielson et al, "Absolute optical ranging using low coherence interferometry", Appl. Opt. 30, 2975 (1991), the so-called "phase slope" (i.e., the slope of the phase function relative to frequency) provides an accurate measure of the optical path length which again is the product of the index of refraction and of the geometric path length.

Figure 7B:
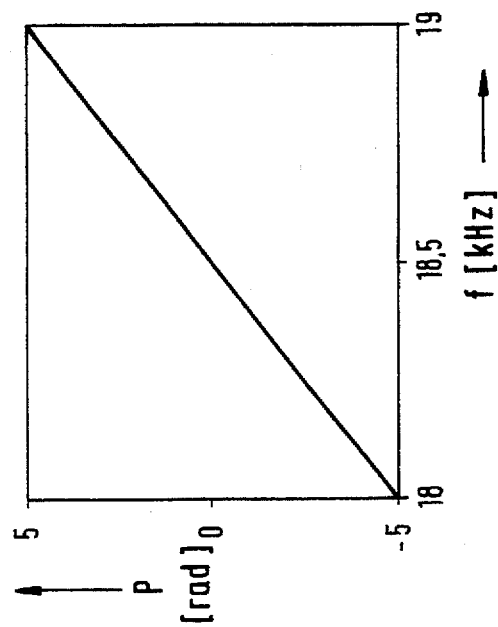
Figure 7A:
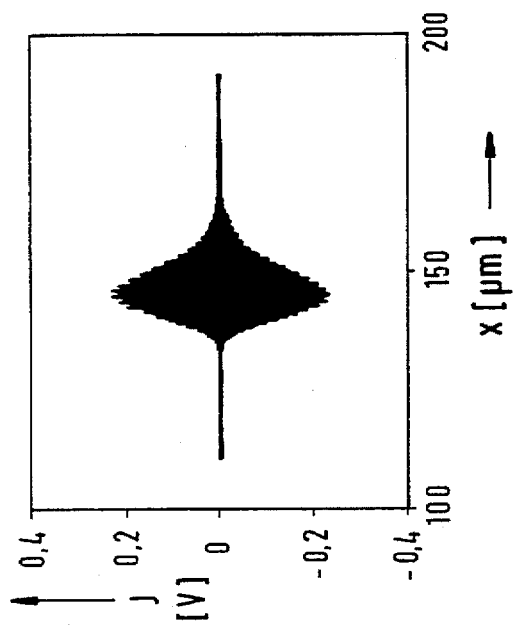

FIG. 7 shows the dependency of the phase (measured in rad) obtained by FFT from the two interferograms of FIG. 5 on the frequency (in kHz) plotted on the abscissa. The slope of the straight line is the phase slope (PS). According to the Danielson publication, the index of refraction is directly obtained from the difference of phase slopes (DPS) of the two PS values at the reflection sites A and B by the following expression $$n = v/\pi \cdot l_g \cdot DPS \qquad (1)$$

where v is the speed of reflector displacement and $l_g$ is the total geometric path length (twice the distance between A and B).

The index of refraction n may be determined in this manner as a measure of the glucose concentration. The measurement quantity obtained from the light (that is, the quantifiable light parameter correlating with glucose concentration) is the DPS value. The correlation between the DPS values measured for various glucose concentrations and the glucose concentration is shown in a log-log plot in FIG. 8, DPS being the ordinate and the concentration C being the abscissa. The data plotted in FIG. 8 denote measured values for seven glucose concentrations, each measured with 32 scans within twenty seconds. The crosses denote error limits of this measurement. The solid line is a best linear fit for all measurements. The curvature at low values arises because the fit does not precisely pass through zero.

The fit corresponds to a change in the DPS value per unit change in the glucose concentration of $2.055 \times 10^{-5}$ rad/Hz per mM glucose. From eq. (1), a change in index of refraction per unit glucose concentration of $2.58 \times 10^{-5}$ per mM can be computed. This result corresponds with good accuracy to conventionally measured values of this magnitude.

When performing measurements on the skin surface, an essentially constant length of the primary-side and of the secondary-side measuring light path may be achieved by pressing the measuring head 13 (FIG. 1) at uniform pressure against the skin. This is not acceptable when applied to the eye. Accordingly a contactless procedure is preferred, that is, the irradiation means by which the measuring light is irradiated from the SCRI into the eye is mounted at a spacing as constant as possible from the eye. This constant spacing may for example be achieved by conventional ophthalmological means, for instance a corresponding face mask (see for instance the European patent document EP 0 603 658 A1). However the incurred and inevitable fluctuations are generally too large to take interferograms which can be used for glucose analysis absent additional measures.

Accordingly, as described above, preferably interferograms from two reflections in the eye are measured, the site of the first reflection being in front of the anterior chamber (on its side away from the eyeball), the second reflection site being behind the anterior chamber (on its side facing the eyeball). Preferably the site of the first reflection is located at the boundary surface 52a of the cornea 52 wetted by the aqueous humor, whereas the site of the second reflection is located at the surface of the eye lens 58 wetted by the aqueous humor. Alternatively the first reflection site also may be located on the outer cornea surface, whereas the second reflection site alternatively may be located at the iris surface or also in the lens. Basically a reflection site more deeply located in the eye, for instance at the retina surface, is possible too.

The above results show that the index of refraction and hence the glucose concentration of the aqueous humor of the eye's anterior chamber can be determined with good accuracy from interferograms. The detection limit of low glucose concentrations essentially depends on the signal-to-noise ratio (SNR) of the measurement. It can be reduced by measurement-technology optimization to such an extent that the full physiological range of glucose concentrations can be analyzed.

Regarding measurements on the living eye, it must be assumed, contrary to the experimental model of FIG. 4 that the geometric light path length $l_g$ is not long-term constant but varies on account of slight deformations of the anterior chamber 54. In this case it is favorable if the index of refraction, i.e. the glucose concentration, can be determined regardless of the fluctuations of the thickness of the anterior chamber and hence fluctuations in the geometric light path in the sample which take place in the living human eye. This can be done when measuring two different light wavelengths on the basis of the following considerations:

For a glucose-water solution, the DPS for each wavelength may be stated as follows, $$DPS_1 = (n_{w1} + c \cdot dn_{g1}) l_g \cdot K \qquad (2)$$

$$DPS_2 = (n_{w2} + c \cdot dn_{g2}) l_g \cdot K$$

The indices 1 and 2 denote the two wavelengths; $n_w$ is the index of refraction of water and $dn_{gi}$ is the incremental change in the index of refraction per unit glucose concentration; c is the glucose concentration and K is a constant.

If, with respect to DPS, an arbitrary glucose concentration (for instance of 5 mM) is standardized as zero, the formulas (2) for relatively small (percentagewise) variations $dl_g$ in the geometric path length $l_g$ may be rewritten as $$DPS_1 = (dl_g \cdot n_{w1} + c \cdot l_g \cdot dn_{g1}) \cdot K \qquad (3)$$

$$DPS_2 = (dl_g \cdot n_{w2} + c \cdot l_g \cdot dn_{g2}) \cdot K$$

These equations can be easily solved for c, the unknown change $dl_g$ of the geometric path length $l_g$ dropping out, hence $$c = \frac{DPS_1 - (n_{w1}/n_{w2}) \cdot DPS_2}{K \cdot l_g [dn_{g1} - (n_{w1}/n_{w2}) dn_{g2}]} \qquad (4)$$

The geometric path length $l_g$ still contained therein is the average value of this quantity without regard to the percentage-wise small fluctuations $dl_g$. This average value can be determined with adequate accuracy from the relative position of the two interferograms (while taking into account an average index of refraction). The accuracy of this determination is higher than the accuracy requirements in clinically determination of glucose concentrations. Therefore the glucose concentration may be determined using a one-point calibration, the patient determining the blood glucose concentration by a conventional procedure and in a single step (appropriately repeated from time to time). In principle the described method even offers the possibility to determine the absolute index of refraction and hence the glucose concentration without calibration.

Figure 9:
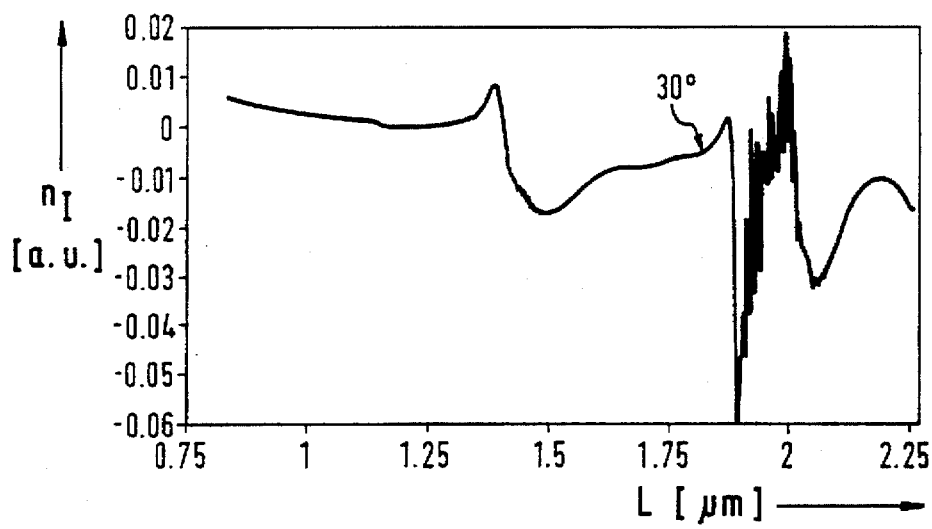
FIG. 9 is a graphical representation of the incremental index of refraction of a glucose solution with respect to pure water versus the light wavelength.
Figure 10:
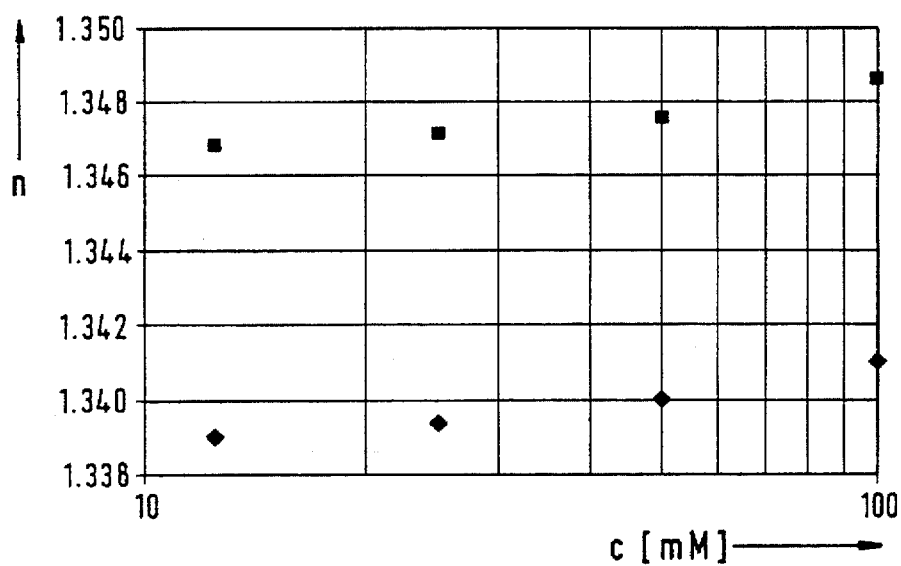
FIG. 10 is a graphical representation of the index of refraction measured according to the invention versus the glucose concentration for two different light wavelength.
Figure 11:
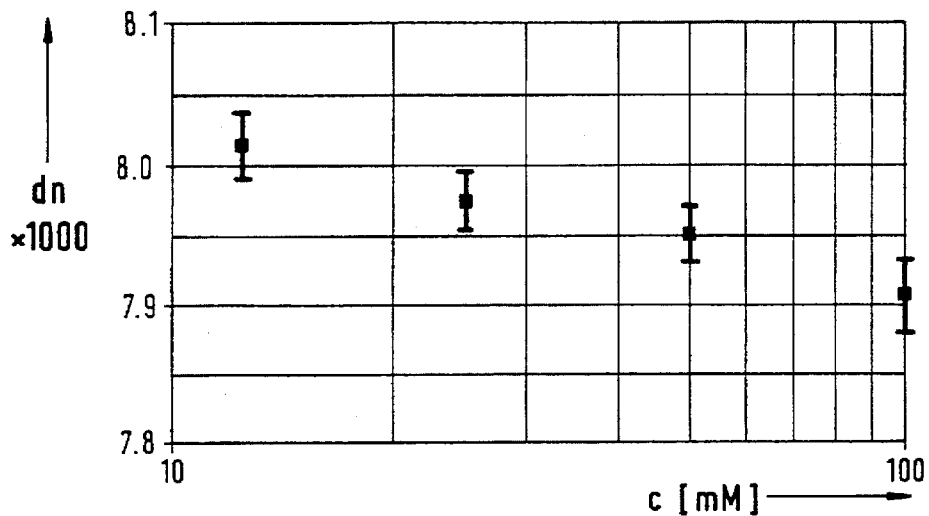
FIG. 11 is a graphical representation of the differential index of refraction of the two wavelengths according to FIG. 10 versus the glucose concentration.

FIGS. 9 to 11 show experimental data concerning the dependence of the index of refraction on the light wavelength and the experimental use of this effect within the scope of this invention.

FIG. 9 shows the incremental index of refraction ($n_r$) of a glucose solution with respect to water, i.e. the difference of the index of refraction of a glucose solution minus the index of refraction of water. $n_r$ is represented in arbitrary units (a.u.) over the light wavelength L (in µm). This graphical representation makes apparent that the index of refraction changes relatively drastically in a certain range of wavelengths. Based on such experimental results a skilled person can select a suitable pair of wavelengths. The difference of the indices of refraction for such pair preferably should be as large as possible.

The maximum which is visible in FIG. 9 at about 1450 nm is due to the displacement of water by glucose in the range of a water absorption band. The slight shoulder at about 1570 nm is caused by a glucose absorption band. This difference could possibly be used as an additional means for separating the influence of glucose as compared to other parameters.

Based on the measurements represented in FIG. 9 experimental work was performed using an experimental model of the anterior chamber corresponding to FIG. 5. Here however the presumption was made that the length of the cuvette k is not known or changes in an unknown manner.

The results of these experiments are shown in FIG. 10 and 11. FIG. 10 shows the change of the index of refraction n with respect to the glucose concentration for the two light wavelengths represented in the figure (1300 and 1550 nm), depending on the glucose concentration which is indicated in mM. The shown values of the index of refraction were calculated from DPS-values using formula (1) (as described in the context of FIGS. 6 and 7). A normalization was performed using values of the index of refraction of pure water which are known from the literature whereby knowledge of $l_g$ is not required.

FIG. 11 is a representation of the dependence of the difference dn of the measurement values of FIG. 10 including error bars on the glucose concentration. It is apparent that the differential index of refraction dn has a clearly measurable dependence on the glucose concentration. The accuracy of the measurement of dn is largely independent on small changes of the geometrical path length (i.e. the length of the cuvette k). Therefore dn is a suitable measurement quantity for the determination of the glucose concentration in cases, where the geometrical path length of the sample light path is not constant.

Even though the above discussed principle of measurement (contrary to the case of conventional spectroscopic measurement) does not mandate detection steps for a plurality of light wavelengths, it may be advantageous to irradiate measuring light with a plurality of different wavelengths and to evaluate the then detected light each time in the above described manner. It may be appropriate furthermore to combine the described method with optical-absorption measurements. As a result accuracy of measurement may be increased, thereby reducing in particular spuriousness of the measurement results on account of further substances contained in the aqueous humor, for instance ascorbic acid, amino acids and lactic acid, that might hamper glucose determination. Moreover the measurement error linked to temperature fluctuations in the eye's anterior chamber may thus be reduced.

We claim:

1. A method for analytically determining a concentration of glucose in a biological sample, said method comprising the steps of:

irradiating light along a primary-side measuring light path into the biological sample;

guiding secondary light emerging from the sample along a secondary-side measuring light path to a photodetector;

detecting the secondary light with the photodetector, the photodetector providing a signal representative of the secondary light, wherein a first portion of the primary light emitted by the light source is guided to the photodetector along a total measuring light path which includes the primary-side measuring light path, an interior light path in which the light travels inside the sample, and the secondary-side measuring light path, wherein a second portion of the primary light emitted by the light source is guided along a reference light path to the photodetector, said reference light path not including an interior light path in which the light travels inside the sample, and wherein the secondary-side measuring light path and the reference light path are combined whereby the secondary light and the reference light interfere with each other such that the photodetector detects an interference signal, said method further comprising the step of determining the glucose concentration based on the signal provided in the detecting step, wherein a factor in the determining of the glucose concentration is an optical light path length of the interior light path inside the sample derived from said interference signal.

2. Method according to claim 1, wherein the optical path length of at least one of the light paths is modulated by a modulating signal and the interference signal is evaluated using the modulation signal.

3. Method according to claim 2, wherein at least two detection steps are performed with two different measuring-light wavelengths to determine a glucose concentration and wherein the wavelength-dependency of the interference signal is used in an evaluation step for said determination.

4. Method according to claim 3, wherein the optical path length of the reference light path is variable and is set to a plurality of lengths, wherein the light source emits a broadband spectrum and in that the wavelength-dependency is determined by means of a Fourier-Transform-Spectroscopy procedure.

5. Method according to claim 1, wherein the light on the reference light path is reflected by a light reflecting optical component into the opposite direction.

6. Method according to claim 1, wherein the optical path length of at least one of the light paths is variable and is set to a plurality of different lengths.

7. Method according to claim 6, wherein the optical path length of the reference light path is variable and is set to a plurality of lengths.

8. Method according to claim 7, wherein the optical path length is varied by moving a reflecting optical element.

9. Method according to claim 6, wherein the optical light path length is varied in an oscillating manner.

10. Method according to claim 1, wherein the light source emits light of a short length of coherence of at most 50µ.

11. A method according to claim 10, wherein the short length of coherence is no greater than 10µ.

12. Method according to claim 10, wherein the primary-side measuring light path and the secondary-side measuring light path run in the same half-space defined by a boundary surface of the sample, whereby the light reflected by the sample enters the secondary-side measuring light path.

13. Method according to claim 12, wherein the primary-side measuring light path and the secondary-side measuring light path partially coincide and wherein an optic coupler is used to split the primary-side sample light path and the reference light path and to combine the secondary-side measuring light path and the reference light path.

14. Method according to claim 12, wherein in order to determine a glucose concentration, several different relations of the path lengths of the total measuring light path in relation to the reference light path are set, where the optical path length of the reference light path is larger than the sum of the optical path lengths of the primary-side measuring light path and the secondary-side measuring light path, whereby the interference signal corresponds to reflections at different depths in the sample.

15. Method according to claim 14, wherein the glucose concentration is determined from the intensity of the interference signal on the set relation of the optical path lengths.

16. Method according to claim 12, wherein the measuring light is irradiated through the eye cornea into the anterior chamber and is detected following reflection in the eye by means of the light emerging through the cornea whereby the sample light path runs from an irradiation site at the cornea through the anterior chamber up to a reflection site and from there to an exit site at the cornea.

17. Method according to claim 16, wherein interferograms of two reflections in the eye are measured, the site of a first reflection being in front of the anterior chamber and the site of the second reflection being located behind the anterior chamber and the glucose concentration is determined in the evaluation step from the two interferograms.

18. Method according to claim 17, wherein the site of the first reflection is located at the boundary surface of the eye cornea wetted by the aqueous humor.

19. Method according to claim 17, wherein the site of the second reflection is located at the boundary of the anterior chamber facing the eye ball.

20. Method according to claim 19, wherein the site of the second reflection is located at the lens surface of the eye lens.

21. Method according to claim 1, wherein the temperature of the biological sample is measured and taken into account in the evaluation step for the determination of the glucose concentration.

22. Method according to claim 1, wherein the biological sample is a biological fluid.

23. A method according to claim 22, wherein the biological fluid comprises blood.

24. Method according to claim 1, wherein the biological sample is a biological tissue.

25. Method according to claim 24, wherein the biological tissue is one of a finger pad, an upper abdominal wall, a nail bed, a lip, a tongue, an inner upper arm of a human, tissue of the sclera and a retina.

26. Method according to claim 1, wherein the biological sample includes the aqueous humor of the anterior chamber of the eye.

27. A method for analytically determining a concentration of glucose as recited in claim 1, wherein said step of determining glucose concentration is based upon a change of an optical path length inside the sample in relation to a given geometrical path length.

28. Glucose-measuring apparatus for the analytical determination of the concentration of glucose in a biological sample, said apparatus comprising:

a light source for emitting measuring light;

light-irradiation means having a light aperture by means of which the measuring light is irradiated through a boundary surface of the sample into said sample;

a primary-side measuring light path from the light emitter to the boundary surface, light detection means for detecting light emerging from the sample at a boundary surface after interaction with the sample; and a secondary-side measuring light path from the boundary surface where the measuring light emerges from the sample to a photodetector, wherein a reference light path of defined optical length is provided for guiding light from the light source to the photodetector, and wherein an optic coupler is positioned in the secondary-side measuring light path by means of which the secondary-side measuring light path and the reference light path are combined in such manner that they are incident at the same point on the photodetector, thereby generating an interference signal, said apparatus further comprising means for determining the glucose concentration based on a signal provided by the light detection means, wherein a factor in determining the glucose concentration is an optical light path length of the secondary-side measuring light path inside the sample derived from the interference signal.

29. Glucose measuring apparatus according to claim 28, wherein the light is guided at least along a part of the light paths in single mode optical fibers.

30. Glucose measuring apparatus according to claim 28, wherein the light source (10) is a light emitting diode.

31. A glucose measuring apparatus according to claim 30, wherein the light emitting diode comprises a superluminescent diode.

32. Glucose measuring apparatus according to claim 28, wherein the primary-side measuring light path and the secondary-side measuring light path partly coincide and pass through the same components.

33. Glucose measuring apparatus according to claim 28, wherein the reference light path comprises a reflecting optical component which is movable along the optical axis for adjusting the optical path length thereof.

34. A method for analytically determining a concentration of glucose in a biological sample, said method comprising the steps of:

irradiating light along a primary-side measuring light path into the biological sample;

guiding secondary light emerging from the sample along a secondary-side measuring light path to a photodetector;

detecting the secondary light with the photodetector, the photodetector providing a signal representative of the secondary light, wherein a first portion of the primary light emitted by the light source is guided to the photodetector along a total measuring light path which includes the primary-side measuring light path, an interior light path in which the light travels inside the sample, and the secondary-side measuring light path, wherein a second portion of the primary light emitted by the light source is guided along a reference light path to the photodetector, said reference light path not including an interior light path in which the light travels inside the sample, wherein the optical path length of at least one of the light paths is variable and is set to a plurality of different lengths, wherein the primary-side measuring light path and the secondary-side measuring light path run in a same half-space defined by a boundary surface of the sample, such that the light reflected by the sample enters the secondary-side measuring light path, wherein the light on the reference light path is reflected by a light reflecting optical component in an opposite direction, and wherein the secondary-side measuring light path and the reference light path are combined such that the secondary light and the reference light interfere with each other such that the photodetector detects an interference signal, said method further comprising the step of determining the glucose concentration based on the signal provided in the detecting step, wherein a factor in said determining of the glucose concentration is an optical light path length of the interior light path inside the sample derived from said interference signal, wherein said determining step includes setting of a plurality of different relations of the path lengths of the total measuring light path in relation to the reference light path, wherein the optical path length of the reference light path is larger than the sum of the optical path lengths of the primary-side measuring light path and the secondary-side measuring light path, whereby the interference signal corresponds to reflections at different depths in the sample, and determining the glucose concentration from the dependence of the intensity of the interference signal on the set relation of the optical path lengths.

35. A method according to claim 34, wherein the optical path length of at least one of the light paths is modulated by a modulating signal, and the interference signal is evaluated using the modulation signal.

36. A method according to claim 35, wherein at least two detection steps are performed with two different measuring-light wavelengths to determine a glucose concentration, and wherein the wavelength-dependency of the interference signal is used in an evaluation step for said determination.

37. A method according to claim 34, wherein the optical path length of the reference light path is variable, and is set to a plurality of lengths.

38. A method according to claim 37, wherein the optical path length is varied by moving the reflecting optical component.

39. A method according to claim 34, wherein the optical light path length is varied in an oscillating manner.

40. A method according to claim 34, wherein the light source emits light of a short length of coherence of no greater than 50μ.

41. A method according to claim 40, wherein said short length of coherence is no greater than 10μ.

42. A method according to claim 34, wherein an optic coupler is used to split the primary-side sample light path and the reference light path and to combine the secondary-side measuring light path and the reference light path.

43. A method according to claim 34, wherein the temperature of the biological sample is measured and taken into account in the evaluation step for the determination of the glucose concentration.

44. A method according to claim 34, wherein the biological sample is a biological fluid.

45. A method according to claim 34, wherein the biological sample is a biological tissue.

46. A method according to claim 45, wherein the biological tissue is one of a finger pad, an upper abdominal wall, a nail bed, a lip, a tongue, an inner upper arm of a human, tissue of the sclera, and a retina.

* * * * *